United States Patent [19]
Furst et al.

[11] Patent Number: 5,325,713
[45] Date of Patent: Jul. 5, 1994

[54] APPARATUS AND METHOD FOR DETERMINING THE INTEGRITY OF COATED PAPER

[75] Inventors: Kenneth L. Furst, Appleton, Wis.; Robert O. Dilmore, Ross Township, Allegheny County, Pa.; Milan D. Janic, Columbus, Ohio; Bozidar Stipanovic, Lake Forest, Ill.

[73] Assignee: PPG Industries, Inc., Pittsburgh, Pa.

[21] Appl. No.: 54,631

[22] Filed: Apr. 29, 1993

[51] Int. Cl.⁵ .................. G01N 33/34; G01B 17/00
[52] U.S. Cl. ............................................ 73/150 R
[58] Field of Search .................. 73/866, 150, 7; 118/712, 713, 714, 57; 427/8, 9, 10

[56] References Cited

U.S. PATENT DOCUMENTS

| | | | |
|---|---|---|---|
| 2,734,375 | 2/1956 | Galbraith et al. | 73/150 R |
| 3,040,559 | 6/1962 | Adams | 73/7 |
| 3,063,285 | 11/1962 | Jensen et al. | 73/150 R |
| 3,129,586 | 4/1964 | Allen et al. | 73/150 R |
| 3,788,137 | 1/1974 | Lyon et al. | 73/150 R |

OTHER PUBLICATIONS

"TAPPI Control Methods", RC-183, RD-185, Jan. 1953, Technical Association of the Pulp and Paper Industry.

Primary Examiner—Hezron E. Williams
Assistant Examiner—Michael Brock
Attorney, Agent, or Firm—Irwin M. Stein

[57] ABSTRACT

Described is apparatus and a method for measuring the integrity of coated paper, which apparatus comprises, a reservoir for a test liquid, e.g., water, retaining means for holding a sample of coated paper which is in liquid communication with the test liquid reservoir, means for applying ultrasonic energy to the sample of coated paper, photoelectric means for continuously measuring the turbidity of the test liquid, the photoelectric means being in liquid communication with the test liquid reservoir and the paper sample, recording means electrically connected to the photoelectric means for continuously recording the turbidity measurements, and means, including pumping means, for circulating test liquid between the reservoir, photoelectric means and paper sample retaining device.

16 Claims, 1 Drawing Sheet

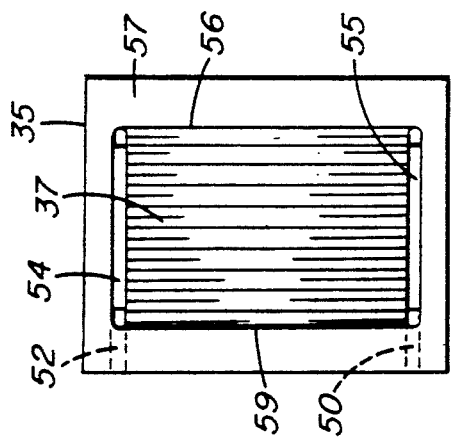
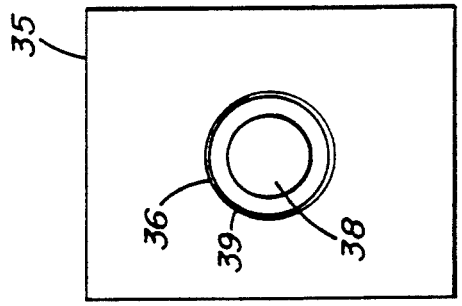
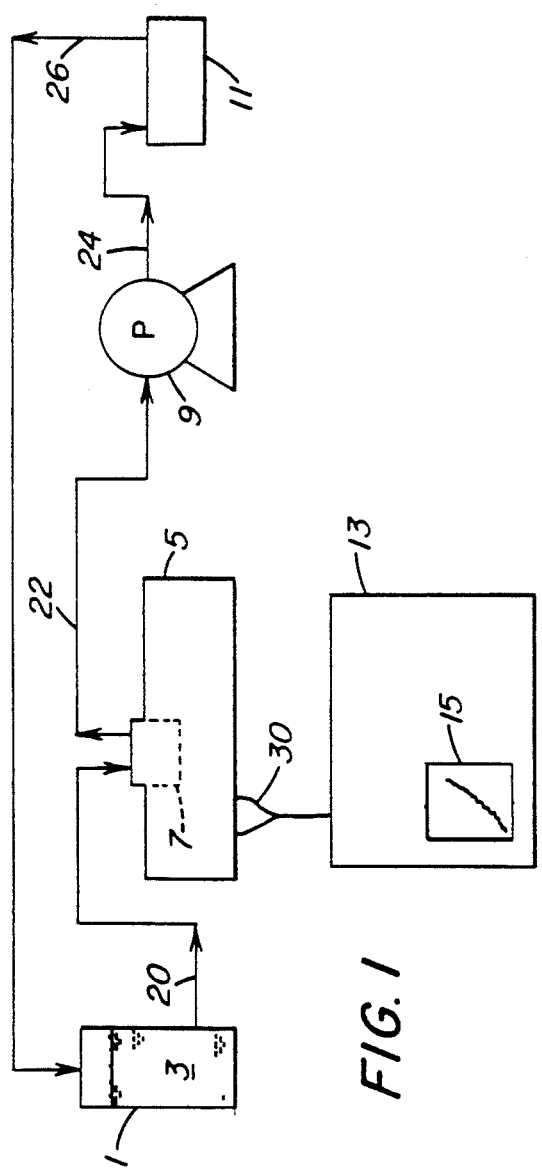
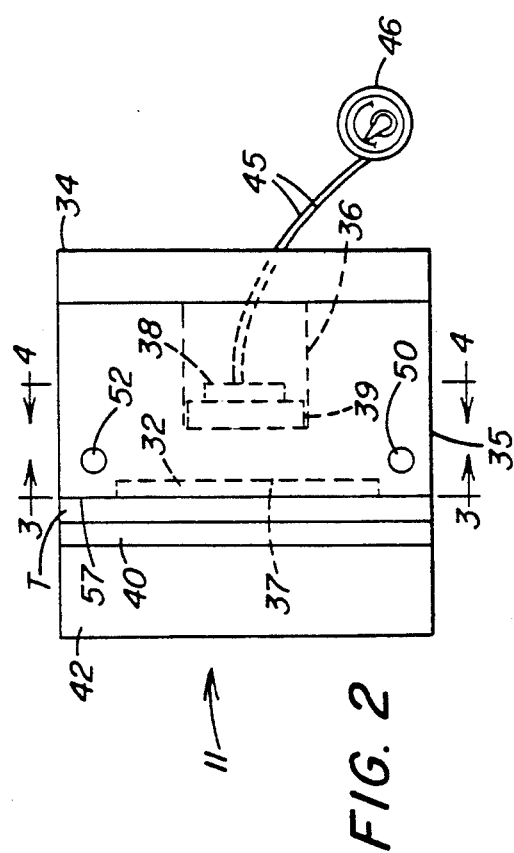

APPARATUS AND METHOD FOR DETERMINING THE INTEGRITY OF COATED PAPER

DESCRIPTION OF THE INVENTION

The surface(s) of many grades of paper, particularly printing paper grades, are commonly coated with a layer of pigment particles held together by means of a crosslinked polymeric binder system. The coatings are generally designed to mask or change the appearance of the paper base stock, improve opacity and import a smooth and receptive surface for printing. The pigments typically used in the paper coating are clay, calcium carbonate, titanium dioxide, silica and plastic pigments, such as polystyrene. The adhesives typically used to bind the pigments are typically starches, proteins, such as casein and soya protein, and synthetic binders, such as styrene-butadiene latices, acrylics and polyvinyl alcohol. The binder system may also include additives, such as insolubilizers, plasticizers, such as stearates and wax emulsions, thickeners, dispersants, preservatives, defoamers and dyes.

The pigment particles in the coating are held by the binders, such as starches, proteins, and synthetic latices in the coating. During lithographic printing the surface of the paper is wet by the printing roll surface conditioners referred to as fountain solutions. Fountain solutions are typically solutions of water, solvents, such as butyl cellusolve or isopropyl alcohol, and selected nonionic surfactants. The paper surface may absorb the fountain solution, weakening the binder in the coating. Subsequent printing operations apply tack forces to the surface of the coating sufficient to pick out the coating, if the binders have weakened sufficiently. Starches are particularly susceptible to weakening with the absorption of fountain solutions. It is, therefore, important for the paper industry to have some knowledge and measure of the integrity of the coating that is experiencing wet shear. Knowledge of the integrity of the coating allows correlation to other properties of the coated paper, such as its behavior during printing.

A number of methods are used in the paper industry to measure the resistance of a paper coating to removal by abrasion. The wet finger test (Method 468) and the Taber Abrader Test (Method 462) are examples of two TAPPI Useful Methods. Method 468 specifies immersing a sheet of coated paper in water and rubbing until a softening of the coating is noted. Method 462 specifies clamping the sample on a turntable, immersing the sample with water and rubbing the surface with a stationary brush. The amount of coating loss in a set time is indicated by the turbidity of the water suspension. Another common method used in the paper industry is the Adams Wet Rub Test, in which a moistened rubber roll against the sample (mounted on a backing roll) for a specified time and at a known pressure. The amount of coating removed is determined by measuring the turbidity of a given volume of water containing the removed coating.

Some of the aforedescribed methods are subjective (Method 468) while others provide only one data point, i.e., the end point, which is taken as a measure of the paper's coating resistance toward rubbing.

An apparatus and method has now been developed which continuously measures the loss of coating over time. This apparatus is capable of delivering more meaningful information relating to the measure of the integrity of the paper coating, which then can be correlated to the printability of the coated paper. Moreover, this test may be useful for a broader physical and chemical study of the coated paper system. More particularly, the apparatus, which is described in more detail hereinafter, comprises in combination a reservoir for water, a device for retaining a sample of coated paper, means for applying ultrasonic energy to the sample of coated paper, photoelectric means for continuously measuring the turbidity of water, recording means electronically connected to the photoelectric means for continuously recording the turbidity measurements, and means, including pumping means, for circulating water to the water reservoir, the photoelectric means, the device for holding the paper sample, and for returning the water to the reservoir.

BRIEF DESCRIPTION OF THE DRAWINGS

The present invention will be more fully understood by reference to the following description and drawings wherein:

FIG. 1 is a schematic of the individual principal components comprising the apparatus of the present invention;

FIG. 2 is an enlarged side view of component 11 (sample retaining device) of FIG. 1;

FIG. 3 is an enlarged end view of component 11 taken at Section Line 3—3 in FIG. 2; and FIG. 4 is an enlarged end view of component 11 shown in FIG. 2 taken at Section Line 4—4.

DETAILED DESCRIPTION OF THE INVENTION

Referring now to FIG. 1, there is shown a schematic of the principal components of the apparatus of the present invention. Reference 1 is a reservoir for a suitable testing liquid 3. Typically, the testing liquid is deionized water, but may be any other suitable liquid, such as offset printing fountain solutions. The amount of liquid 3 used in the method of the present invention is that amount required to fill the liquid volume of the photoelectric cell 7, pump 9, sample retaining means 11 and all connecting conduits, i.e., so that no air or gas is aspirated into the system by pump 9 during operation of the apparatus. The reservoir may be fabricated from any suitable material, e.g., glass, plastic or metal.

Testing fluid 3 as shown is withdrawn from reservoir 1 and forwarded by means of conduit 20 to continuous flow photoelectric cell 7 in turbidimeter 5 from whence the test liquid, e.g., water, is forwarded by means of conduit 22 to pump 9, e.g., a peristaltic pump, and thence by conduit 24 to paper sample retaining device 11 wherein the test liquid contacts the coated paper sample. From sample retaining device 11, test liquid is returned by conduit 26 back to reservoir 1.

In sample retaining device 11, ultrasonic energy is applied to the paper sample, as described hereinafter, while simultaneously contacting the coating of the paper sample with test liquid. As a result of the impact of ultrasonic energy and the movement of circulating test water across the coating surface of the paper sample, coating material is gradually removed from the paper, which causes the turbidity of the circulating test liquid to increase. The increase in turbidity is continuously measured by photoelectric cell 7 and recorded in recording means 13, which is connected electronically to turbidimeter 5. As shown, data obtained from turbidimeter 5 may be displayed on strip chart 15 of recording means 13, thereby to provide a continuous physical display of the destruction of the coating.

Turbidimeter 5 may be any conventionally available turbidimeter capable of being equipped with a continuous flow photoelectric cell 7. More particularly, a nephelometer is used to measure directly the intensity or transmission of the light source used in instrument 5. Turbidimeter 5 is electronically connected to instrument recording means 13 by signal carrying means 30 for continuously recording the turbidity measurements obtained by the photoelectric cell 7. As shown, a conventional strip chart 15 is displayed. However, recording means 13 may comprise an electronic digital computer and monitor (not shown), which can both store the data and display it on a monitor. In using electronic digital computer means for recording the data obtained by photoelectric cell 7, the computer may be equipped with a conventional A-D board to convert the analog signals from the turbidimeter to digital readings that may be processed by an appropriately programmed computer. The digital signal from the A-D board may be converted by the computer to processable data by conventional spread sheet software. In that case, the computer and its attendant software can process the turbidity data and provide a continuous display of data on a monitor screen in tabular or graphical form. Such data can, of course, be printed on conventional printers electronically connected to the computer or stored in a data base for later processing.

Pump 9 may be any conventional positive displacement pump, e.g., a peristaltic pump, capable of handling the relatively low volumes of test liquid required to practice the method. Preferably, the pump does not require priming and does not cause cavitation or incorporation of air into the circulating test liquid. As shown, the components of the present apparatus are depicted as separate components; however, such components may be assembled and incorporated into a single unit for ease of transportation and use. In addition, although the sequence of test liquid flow is shown as moving from the liquid reservoir to the turbidimeter and thence through the pump and sample retaining device, it is clear that the arrangement of components may be altered to provide a different sequence of flow.

Conduits 20, 22, 24 and 26 may be of any standard conventional connecting tubing, such as rubber tubing or Tygon® tubing. Such tubing should be made of material which does not erode and introduce particles of the tubing into the circulating test liquid so that the turbidity readings made by the photoelectric cell accurately depict the amount of material released from the paper coating.

Referring now to FIG. 2, there is shown an enlarged side view of a preferred embodiment of sample retaining means 11, which may take any geometric shape provided that it allows the application of ultrasonic energy to the sample of paper while simultaneously passing test liquid uniformly across the surface of the coating. FIGS. 3 and 4 illustrate end views of device 11 taken respectively at section lines 3—3 and 4—4.

Sample retaining means 11 may be constructed of any suitable material that is resistant to erosion from the test liquid and material eroded from the coating. Stainless steel or aluminum are contemplated for use for device 11; however, it may be fabricated also from a suitable machinable plastic.

Sample retaining means 11 as shown comprises substantially rectangular housing member 35 in the form of a plate having parallel major surfaces defining a front side and back side. The front side comprises a shoulder 57, which circumscribes the perimeter of the surface of the rectangular front side of member 35, and a second planar surface 37 offset (recessed) from the front side and substantially parallel to said front side. While shown in substantially rectangular shape, component 11 may taken any convenient geometric shape, e.g., a square shape, as long as it provides means for retaining the paper sample, means for simultaneously applying ultrasonic energy to the paper sample and means for flowing test liquid uniformly over the surface of the coating on the paper sample.

Shoulder 57, surface 37 and channels 54 and 55 define a recessed shallow chamber 32 within the center of the front side of housing member 35. Chamber 32 is recessed to a depth sufficient to allow the test liquid, e.g., water, to pass uniformly over surface 37, i.e., between surface 37 and the sample of paper T, which is placed upon and supported by shoulder 57. As contemplated herein, surface 37 is recessed from about 1/16 inch to ⅛ inch (0.16 centimeters–0.32 centimeter) below the level of the front face of body 35. It is preferred that the volume of chamber 32 not be too large since increasing the volume only serves to increase the volume of test liquid required.

Surface 37 may be smooth or may be groove, channeled, waffled, etc., as shown in FIG. 3. As depicted in FIG. 3, surface 37 abuts the major sides of the shallow chamber below shoulder 57, as indicated by the numerals 56 and 59, and extends lengthwise to the edge of opposing channels 54 and 55, which are offset (recessed) from surface 37. Channels 54 and 55 are in liquid communication with inlet port 50 and outlet port 52.

The surface of the test paper T exposed to chamber 32 is preferably an area of about 9 square inches (0.0058 square meters), which corresponds to the test area of paper used in the conventional Adams Wet Rub Test. However, any suitable paper test surface area may be used, e.g., from 8 to 9 square inches (0.0052–0.0058 square meters).

Reference numeral 50 indicates an inlet port, which is in liquid communication with channel 55 within member 35. Similarly, reference numeral 52 refers to the outlet port, which is in liquid communication with channel 54. Inlet port 50 and outlet port 52 are threaded to receive male threaded hollow fittings (not shown) for connection to conduits 24 and 26 respectively. The size of channels 55 and 54 are sufficiently large so that there is little or no pressure drop across the length of the channels, i.e., the pressure at the beginning of the channel is substantially the same as at the end of the channel. The absence of a pressure drop assists in providing laminar flow across surface 37 and an even sweep of coating particles off the paper.

The back side of member 35 has a cavity 36, the depth of which extends close to but is spaced from surface 37. In a contemplated embodiment, the bottom surface of cavity 36 extends to within about ⅛ inch (0.32 centimeters) of surface 37. Within cavity 36 is mounted ultrasonic generator 38, which may be a piezoelectric unit. As shown, ultrasonic generator 38 is attached to plate 39, e.g., an aluminum plate, which is adhesively attached to the bottom surface of cavity 36. As shown, cavity 36 is a generally circular or cylindrical cavity. However, it may be of any shape provided that the ultrasonic generator is capable of fitting within cavity 36. The ultrasonic generator is also adhesively attached to plate 39. Ultrasonic generator 37 is connected electrically by suitable electric connections 45 to rheostat 46 which is used to vary the applied input voltage to the ultrasonic generator, thereby varying the intensity of the ultrasonic energy produced. Rheostat 46 receives current from a source of alternating current, not shown.

Referring further to FIG. 2, which illustrates paper sample retaining means 11 in assembled form, there is shown paper sample T mounted upon shoulder 57 of member 35. Paper sample T is positioned in a manner such that the coated surface of the paper sample is in spaced relationship with surface 37, i.e., the paper coating and surface 37 are in a face to face relationship. Abutting paper sample T on the obverse side is gasketing means 40, which provides an airtight seal between the front cover plate 42 and member 35. If the surface of shoulder 57 and the facing surface of front cover page 42 are machined to provide a tight fit, gasket 40 may not be required. Gasket 40 may be made from any suitable material such as rubber. Also shown is back plate 34, which may have small channels (not shown) to allow electrical leads 45 from ultrasonic generator 38 to pass through or around back plate 34. The entire assembly is maintained in a tight coupled relationship by the use of clamps (not shown) that apply pressure to both the front and back plates.

In operation, liquid reservoir 1 is filled with test liquid, e.g., deionized water, in an amount sufficient to fill the entire volume of the system comprising the photoelectric cell, pump, sample retaining device 11 and connecting tubing. The paper sample to be tested is positioned on body member 35 above surface 37 with the coating side facing chamber 32, and gasket 40 applied against the paper sample. Front plate 42 is positioned against rubber gasket 40 and back plate 34, if used, applied against the back side of body member 35. The entire assembly is held together tightly by the use of appropriate clamps.

Ultrasonic generator 38 is turned on and then pump 9 is started. Simultaneously, a timer is started to measure elapsed time. Test water flows from the reservoir 1 to turbidimeter 5 and photoelectric cell 7, though pump 9 and into device 11 through inlet port 50. The test water then enters channel 55, flows across surface 37 and the coated surface of paper sample T, and exits device 11 via channel 54 and outlet port 52, from where it is circulated to reservoir 1. As the coating on the paper is eroded, the turbidity of the circulating water increases.

An initial turbidity reading is recorded when test water first flows through the photoelectric cell, thereby providing a base point. Turbidity data is obtained from turbidimeter 5 which data is transmitted to recording device 13. Values are recorded until the end point of the test, which is arbitrarily chosen and may either be after a preset time or the duration of time required for the turbidity to reach a predetermined NTU value (Nephelometric Turbidity Units).

When the test is completed, all of the powered components are turned off, the paper sample removed from component 11 and the system drained and cleaned. One skilled in the art to which this invention pertains will readily appreciate that modifications, alterations or variations in the components described and their arrangement may be practiced consistent with the teachings of the foregoing description and without departing from the scope of this invention.

EXAMPLE

The coating integrity of three samples of lightweight coated paper sheet was tested in the apparatus of FIG. 1 using deionized water as the test liquid. The paper sample retaining means 11 used was that represented by FIGS. 2, 3 and 4.

The paper samples were prepared by coating groundwood base stock with the coatings described in Table I using a Metalcraft blade coater.

TABLE I

| COATING COMPONENTS | DRY PARTS/100 DRY PARTS PIGMENT | | |
|---|---|---|---|
| | COATING 1 | COATING 2 | COATING 3 |
| #2 Coating clay | 70 | 70 | 70 |
| Delaminated clay | 25 | 25 | 25 |
| Titanium Dioxide | 5 | 5 | 5 |
| Penford 280 starch | 8 | 8 | 8 |
| Dow 640 NA latex | 10 | 10 | 10 |
| Curesan ® 200 Insolubilizer | 0 | 0.16 | 0.64 |
| Calsan ® 50 Lubricant | 0.75 | 0.75 | 0.75 |

A coated sheet (5 inches × 3 inches–12.7 cm × 7.6 cm) from the lightweight coated paper having coating 1 was placed against surface 57 of member 35 of sample retaining means 11 so that the coated surface of the paper faced surface 37. The surface area of the paper sample exposed to water was 8 square inches (0.0052 square meters). The paper sample was held in place by a rubber gasket and a coverplate 42.

The integrity of the coating was tested by setting rheostat 46 to apply 85 volts to the piezoelectric transducer 38, starting the peristaltic pump 9, which produced a flow rate of 500 ml/minute and operating in this manner for a test period of 15 minutes. Turbidity measurements of the circulating deionized water were taken with a Turner nephelometer and recorded on a strip chart recorder.

The test was repeated with the paper samples having coatings 2 and 3. Results are tabulated in Table II, and are compared with Adam Wet Rub Values for the three samples.

TABLE II

| MINUTES | NTU* UNIT READINGS AT INCREMENTAL TIMES | | |
|---|---|---|---|
| | COATING 1 | COATING 2 | COATING 3 |
| 1 | 0 | 0 | 0 |
| 2 | 1 | 0 | 0 |
| 3 | 3 | 1 | 1 |
| 4 | 4 | 2 | 1 |
| 5 | 6 | 3 | 2 |
| 6 | 9 | 5 | 2 |
| 7 | 11 | 7 | 3 |
| 8 | 14 | 10 | 4 |
| 9 | 17 | 12 | 6 |
| 10 | 20 | 15 | 8 |
| 11 | 22 | 19 | 10 |
| 12 | 25 | 22 | 12 |
| 13 | 27 | 25 | 15 |
| 14 | 29 | 29 | 19 |
| 15 | 30 | 33 | 23 |
| Adams Wet Rub | 17.6 | 16.4 | 8.6 |

*Nephelometric Turbidity Units

The invention has been described above with reference to certain embodiments and it is therefore apparent that the preceding description is not exhaustive of all forms which the apparatus and method of the present invention may take. Accordingly, the foregoing description should not be considered as limiting the scope of this invention.

What is claimed is:

1. Apparatus for measuring the integrity of a paper coating comprising, in combination, a reservoir for a test liquid, means for retaining a sample of coated paper, said retaining means being separate from but in liquid communication with said test liquid reservoir, means for applying ultrasonic energy to the sample of coated paper, photoelectric means for continuously measuring the turbidity of the test liquid, said photoelectric means being in liquid communication with said reservoir and said sample retaining means, recording means electronically connected to said photoelectric means for continuously recording said turbidity measurements, and means, including pumping means, for circulating test liquid between said reservoir, said photoelectric means, and said paper sample retaining means.

2. The apparatus of claim 1 wherein said means for applying ultrasonic energy is an ultrasonic transducer.

3. The apparatus of claim 2 wherein the ultrasonic transducer is a piezoelectric transducer.

4. The apparatus of claim 1 wherein the photoelectric means for continuously measuring the turbidity of the water is a Nephelometer.

5. The apparatus of claim 1 wherein the recording means electronically connected to said photoelectric means is a strip chart instrument.

6. The apparatus of claim 1 wherein the recording means electronically connected to said photoelectric means is an electronic digital computer.

7. The apparatus of claim 1 wherein said pumping means is a positive displacement pump.

8. The apparatus of claim 7 wherein said positive displacement pump is a peristaltic pump.

9. The apparatus of claim 1 wherein said sample retaining means comprises a housing member in the form of a plate having substantially parallel surfaces defining a front side and a back side, said front side having a shoulder circumscribing its perimeter and a second planar surface recessed from said shoulder and substantially parallel thereto, said second planar surface having two recessed channels at opposite ends, said shoulder, recessed second planar surface and recessed channels defining a shallow chamber, said housing member having an inlet port communicating with one of said recessed channels and an outlet port communicating with the other of said recessed channels, and a cover plate juxtaposed to said front side of said housing member.

10. The apparatus of claim 9 wherein the sample retaining means further includes gasketing means between said cover plate and said front side of said housing member.

11. The apparatus of claim 9 wherein the back side of said housing member has a cavity for housing said means for applying ultrasonic energy.

12. A method for measuring the integrity of a paper coating on a sample of coated paper, which comprises, in combination, the steps of:
   a. establishing a reservoir of test liquid,
   b. continuously contacting the coating of said paper sample with test liquid from said reservoir while simultaneously applying ultrasonic energy to the surface of said coating,
   c. recirculating test liquid which has contacted said coating to said reservoir, and
   d. continuously measuring the turbidity of the recirculated test liquid.

13. The method of claim 12 wherein the test liquid is water or a fountain solution.

14. The method of claim 12 wherein the test liquid is recirculated using a positive displacement pump.

15. The method of claim 12 wherein the turbidity is measured using a nephelometer.

16. The method of claim 12 wherein the test liquid is deionized water, the coating of said paper sample is contacted with said water by passing the water substantially uniformly across the surface of said coating, ultrasonic energy is applied to said paper sample with a piezoelectric transducer, and the turbidity of the recirculated water is measured using a nephelometer.

* * * * *